United States Patent [19]

Preidel et al.

[11] Patent Number: 5,147,590
[45] Date of Patent: Sep. 15, 1992

[54] METHOD OF MAKING THE ELECTRODE

[75] Inventors: Walter Preidel; Herbert Grossmann, both of Erlangen, Fed. Rep. of Germany

[73] Assignee: Siemens Aktiengesellschaft, Berlin & Munich, Fed. Rep. of Germany

[21] Appl. No.: 691,840

[22] Filed: Apr. 26, 1991

[30] Foreign Application Priority Data

May 2, 1990 [DE] Fed. Rep. of Germany ....... 4014110

[51] Int. Cl.$^5$ ..................... B29C 41/02; C23C 16/00
[52] U.S. Cl. ..................................... 264/81; 264/105; 427/122; 427/249
[58] Field of Search ................. 264/81, 105; 427/122, 427/249

[56] References Cited

U.S. PATENT DOCUMENTS

| | | | |
|---|---|---|---|
| 3,677,795 | 7/1972 | Bokros et al. | 264/81 X |
| 3,943,218 | 3/1976 | Dietze et al. | 264/81 |
| 3,949,106 | 4/1976 | Araki et al. | 427/249 |
| 4,034,031 | 7/1977 | Lersmacher et al. | 264/81 X |
| 4,495,039 | 1/1985 | Cerise et al. | 204/130 |
| 4,612,100 | 9/1986 | Edeling et al. | 204/192 |
| 4,748,983 | 6/1988 | Shigeta et al. | 128/639 |
| 4,773,433 | 9/1988 | Richter et al. | 128/784 |
| 4,813,967 | 3/1989 | Renard et al. | 623/66 |

FOREIGN PATENT DOCUMENTS

| | | |
|---|---|---|
| 0055406 | 7/1982 | European Pat. Off. . |
| 0072359 | 10/1987 | European Pat. Off. . |
| 1062612 | 7/1959 | Fed. Rep. of Germany . |
| 1168315 | 4/1964 | Fed. Rep. of Germany . |
| 2613072 | 10/1977 | Fed. Rep. of Germany . |
| 2613052 | 7/1981 | Fed. Rep. of Germany . |
| 3047805 | 5/1985 | Fed. Rep. of Germany . |
| 3345990 | 6/1985 | Fed. Rep. of Germany . |
| 3628652 | 3/1987 | Fed. Rep. of Germany . |
| WO86/00230 | 1/1986 | PCT Int'l Appl. . |

OTHER PUBLICATIONS

J. C. Bokros, R. J. Akins: "Applications of Pyrolytic Carbon in Artificial Heart Valves: A Status Report", pp. 6–12, General Atomic Company, San Diego, CA, Aug. 12, 1971.

"Med. & Biol. Eng. & Comput.", vol. 17 (1979), pp. 465–470.

*Primary Examiner*—Leo B. Tentoni
*Attorney, Agent, or Firm*—Kenyon & Kenyon

[57] ABSTRACT

An electrode for medical applications can be manufactured with different geometries, and particularly in the form of hollow bodies, by depositing pyrographite on a shaped body of glassy carbon. The deposition is achieved by means of the pyrolysis of hydrocarbons at temperatures ranging approximately from 1800° to 2100° C. After cooling, the pyrographite coating is removed from the shaped body and a pyrographite electrode is produced from the coating.

4 Claims, No Drawings

METHOD OF MAKING THE ELECTRODE

BACKGROUND OF THE INVENTION

The invention relates generally to electrodes for medical applications, and more specifically to a method of manufacturing such an electrode with different geometries, specifically hollow bodies.

Electrodes made of carbon lend themselves particularly well to use in medicine since carbon is a material that is readily tolerated by the human body, i.e. it is body compatible. Of the known carbonaceous materials, pyrocarbon or pyrographite, and glassy carbon enjoy the widest use. For example, German patents 26 13 052 and 26 13 072 disclose such use. This is due especially to the fact that these materials can be activated, that is, they permit the surface of the electrode to be enlarged.

The shape of the electrodes or electrode heads made from the aforesaid carbonaceous materials has up to now been limited largely to a mushroom shape, that is, to a hemispherical geometry. However, full spheres occasionally are also used as electrode tips with these so-called tip electrodes. The reason for these particular geometries is that it is very difficult in practice to realize other electrode shapes, such as tubular shapes or hollow bodies, with these materials. In fact, up to now it has only been possible to produce single electrodes with other geometries on a laboratory scale.

Since suitable carbon electrodes are not currently available for important applications, particularly the bipolar stimulation of the heart, where tubular electrodes are predominantly required, other electrode materials, such as platinum, must be resorted to in such cases. However, this means that different materials have to be used for the two electrodes required with pacemakers, that is, the stimulating electrode and the indifferent electrode. This is undesirable. Besides, in certain fields of application, such as in the case of implantable oxygen sensors, platinum cannot be used.

The present invention is directed to overcoming the problem of developing a method for manufacturing electrodes for medical applications with different geometries, and more particularly as hollow bodies.

SUMMARY OF THE INVENTION

The present invention solves this problem by depositing pyrographite, by means of the pyrolysis of hydrocarbons at temperatures ranging approximately from 1800° to 2100° C., on a shaped body made of glassy carbon that has been annealed at temperatures of up to approximately 2500° C., removing the pyrographite coating from the shaped body after cooling, and producing a pyrographite electrode from it.

The process of the invention makes it possible to manufacture special electrode shapes from carbon in the modification of pyrographite (pyrolytic graphite) that are suitable for use in electromedicine. To this end, glassy carbon which has been heated to temperatures of up to 2500° C. is used as a shaped body or shaped part. On the surface of that shaped body, pyrographite is then deposited in a second high-temperature operation, the operating temperature ranging from approximately 1800° to 2100° C. The pyrolysis gas used is a hydrocarbon, preferably methane. The rate of deposition is usually about 1 micron/minute. For the electrodes being manufactured, a coating thickness greater than 0.1 mm is generally required. A thickness of about 0.2 mm, for example, will suffice.

When the desired coating thickness has been obtained and the shaped body is completely covered by a coating of pyrographite, the deposition, that is, the pyrolytic process, is terminated, followed by cooling. After cooling, the pyrographite coating is removed from the shaped glass-carbon body. The separation of shaped body and coating can be readily effected because there is no interaction between glassy carbon and pyrographite even at elevated temperatures. Moreover, a slightly greater coefficient of expansion of the shaped glass-carbon body has a beneficial effect on the separation. For the production of tubular pyrographite coatings, glass-carbon rods, from which the coating is stripped after cooling, have proved advantageous.

The electrode blank removed from the shaped body is then processed into pyrographite electrodes. To this end, the pyrographite body may be machined. For example, sleeve-like sections may be cut from a graphite tube and then used as cylindrical electrodes with an open cross-sectional area accommodating a cable or wire, for example, for use as indifferent electrodes in the bipolar stimulation of the heart, or as sensor electrodes for an oxygen sensor. The electrodes may further be electroplated with silver at specific points to provide for better contact making. Moreover, the electrode surface may be adapted to a given application, that is, a smooth electrode surface may be roughened, sand-blasted, and activated chemically or electrochemically.

Sleeve-like pyrographite electrodes manufactured by the method of the present invention may be used in the non-activated state as sensor electrodes, particularly in oxygen sensors. In the activated state, such an electrode may be used in place of a platinum electrode as indifferent electrode in the bipolar stimulation of the heart. This offers an advantage, for example, in physiologically controlled pacemakers, which require a lead for the working electrode, i.e. the stimulating electrode, which for example can be a hemispherical glass-carbon electrode. These pacemakers also require a cable for the oxygen-sensor electrode and for the reference electrode. The need for another cable increases the risk factor in the implantation—a more complicated operation, vascular problems, danger of thrombosis, etc. These risks can be eliminated by enclosing the stimulating-electrode cable in sleeve-like electrodes, which can be accomplished by using an inventive pyrographite electrode as the sensor electrode.

DETAILED DESCRIPTION

Glass-carbon rods with an outside diameter of from 1 to 2 mm are annealed at about 2400° C., if this was not already done during their fabrication. Such a material will be stable both mechanically and chemically. The glass-carbon rods are then surface-coated with pyrographite by means of the pyrolysis of methane at about 1900° C. After cooling, the pyrographite coating is stripped from the glass-carbon rods. Pyrographite tubes with an inside diameter of 2 mm and a wall thickness of from 0.15 to 0.2 mm, for example, are so obtained. From these tubes, sleeves are then cut on the lathe and incorporated as electrodes in stimulating-electrode cables, i.e. mounted on the cables, spaced a given distance from the stimulating electrode. In combination with a reference electrode made of Ag/AgCl, for example, such a pyrographite electrode then forms an oxygen sensor, with the stimulating electrode of the pacemaker or the housing of the pacemaker serving as the counter electrode.

A prototype of such an oxygen sensor will have a sleeve-like sensor electrode, for example, with a surface area of 25 mm$^2$, disposed about 3 cm to the rear of a glass-carbon electrode on the stimulating-electrode cable. Such a sensor will have a relatively short response time. It will also have long-term stability, and the fluctuations in the peak values will be relatively minor.

What is claimed is:

1. A method of manufacturing an electrode for medical applications comprising the steps of:
   a) annealing a shaped body of glassy carbon at temperatures of up to approximately 2500° C.;
   b) depositing pyrographite on the shaped body of glassy carbon by means of a pyrolysis of a hydrocarbon at temperatures ranging approximately from 1800° to 2100° C. to form a pyrographite coating;
   c) cooling the shaped body and the pyrographite coating;
   d) removing the pyrographite coating from the shaped body; and
   e) producing the electrode from the pyrographite coating.

2. The method according to claim 1, wherein the hydrocarbon used is methane.

3. The method according to claim 1, wherein the shaped body comprises a glass-carbon rod, and the pyrographite coating comprises a tubular pyrographite coating, and after the step of cooling further comprising the step of removing the tubular pyrographite coating from the glass-carbon rod.

4. The method according to claim 2, wherein the shaped body comprises a glass-carbon rod, and the pyrographite coating comprises a tubular pyrographite coating, and after the step of cooling further comprising the step of removing the tubular pyrographite coating from the glass-carbon rod.

* * * * *

UNITED STATES PATENT AND TRADEMARK OFFICE
CERTIFICATE OF CORRECTION

PATENT NO. : 5,147,590

DATED : September 15, 1992

INVENTOR(S) : Walter Preidel, et al.

It is certified that error appears in the above-identified patent and that said Letters Patent is hereby corrected as shown below:

On the title page Item "[54]", change title to --METHOD OF MAKING AN ELECTRODE--.

Signed and Sealed this

Nineteenth Day of October, 1993

Attest:

BRUCE LEHMAN

*Attesting Officer*     *Commissioner of Patents and Trademarks*